US008955200B2

(12) United States Patent
Ng (10) Patent No.: US 8,955,200 B2
(45) Date of Patent: Feb. 17, 2015

(54) SECURE ADJUSTABLE ORTHOTIC DEVICE (75) Inventor: Kwok Tim Ng, Hong Kong (CN)

(73) Assignee: Bio Cybernetics International, Inc., La Verne, CA (US)

(*) Notice: Subject to any disclaimer, the term of this patent is extended or adjusted under 35 U.S.C. 154(b) by 551 days.

(21) Appl. No.: 13/364,038

(22) Filed: Feb. 1, 2012

(65) Prior Publication Data

US 2012/0203153 A1    Aug. 9, 2012

Related U.S. Application Data (60) Provisional application No. 61/438,509, filed on Feb. 1, 2011.

(51) Int. Cl.
A44B 11/25    (2006.01)
A61F 5/055    (2006.01)
A43C 11/14    (2006.01)
A61F 5/01    (2006.01)

(52) U.S. Cl.
CPC .............. *A61F 5/055* (2013.01); *A43C 11/148* (2013.01); *A61F 5/01* (2013.01)
USPC ................ 24/168; 24/170; 24/171; 24/190; 24/191

(58) Field of Classification Search
CPC .. A44B 11/25; A44B 11/2526; A44B 11/253; A44B 11/2534; A44B 11/2542; A44B 11/2592
USPC .......... 24/168, 170, 171, 181, 194, 191, 68 E, 24/68 A, 16 PB, 132 R, 132 AA, 645, 593.1, 24/643, 190
See application file for complete search history.

(56) References Cited

U.S. PATENT DOCUMENTS

| 376,055 | A |  | 1/1888 | Hopkins |
|---|---|---|---|---|
| 3,267,545 | A |  | 8/1966 | Eckart |
| 4,406,043 | A |  | 9/1983 | Friedman |
| 4,688,337 | A |  | 8/1987 | Dillner et al. |
| 4,733,440 | A | * | 3/1988 | Ogawa ............................ 24/170 |
| 4,903,381 | A |  | 2/1990 | Fohl |
| 5,572,771 | A |  | 11/1996 | Kelleghan |
| 5,774,953 | A | * | 7/1998 | Mao ........................... 24/579.09 |
| 6,056,712 | A |  | 5/2000 | Grim |
| 7,371,221 | B1 |  | 5/2008 | Baker |
| 7,666,155 | B1 |  | 2/2010 | Jensen et al. |
| 8,439,943 | B2 | * | 5/2013 | Chao .............................. 606/203 |
| 8,448,303 | B1 | * | 5/2013 | Wall ................................ 24/194 |
| 8,650,665 | B2 | * | 2/2014 | Shirai ............................... 2/183 |
| 2006/0135897 | A1 |  | 6/2006 | Dellanno |
| 2006/0293624 | A1 |  | 12/2006 | Enzerink et al. |
| 2009/0094811 | A1 | * | 4/2009 | Young ............................. 24/652 |

(Continued)

FOREIGN PATENT DOCUMENTS

DE    20002436    8/2000

*Primary Examiner* — Robert J Sandy
*Assistant Examiner* — Rowland Do
(74) *Attorney, Agent, or Firm* — Holland & Hart (57) ABSTRACT A secure adjustable orthotic device having multiple brace portions and one or more locking mechanisms. One locking mechanism is a level moving buckle including a top member, a locking member and a base member. The locking member is adapted to engage and disengage an inserted strap in response to the longitudinal movement of the top member relative to the base member. The level moving buckle inhibits accidental longitudinal movement of the inserted strap when the top member is in a locked position.

17 Claims, 10 Drawing Sheets

(56) References Cited

U.S. PATENT DOCUMENTS

| | | |
|---|---|---|
| 2009/0099495 A1 | 4/2009 | Campos et al. |
| 2009/0099562 A1 | 4/2009 | Ingimudarson et al. |
| 2010/0174220 A1 | 7/2010 | Fout et al. |
| 2010/0175232 A1* | 7/2010 | Shirai et al. ............ 24/641 |
| 2010/0286581 A1 | 11/2010 | Hipp et al. |

* cited by examiner

SECURE ADJUSTABLE ORTHOTIC DEVICE

CROSS-REFERENCE TO RELATED APPLICATION

The present application claims priority to U.S. Provisional Application No. 61/438,509, entitled "Secure Adjustable Orthotic Device," filed Feb. 1, 2011, the entire contents of which are herein incorporated by reference.

FIELD OF THE INVENTION

The present invention generally relates to a secure adjustable orthotic device or orthosis (commonly known as a brace or splint) comprising various buckles, straps, and adjustable supports. More particularly, the invention relates to an orthotic device having level moving buckles and secure adjustable supports.

BACKGROUND OF THE INVENTION

In certain orthosis applications, it is important that buckles and adjustable supports be easy to use while also inhibiting the accidental release, tightening or adjustment of an inserted strap (in the case of a buckle) or bracket (in the case of an adjustable support). For example, a common method of alleviating pain, promoting healing, and preventing further injury in patients who have suffered a back or spine injury (or in post-operative spinal surgery patients) is to stabilize the spine by means of an orthotic device. Among other things, an orthosis can provide stabilization, support, protection, pain reduction and replacement of lost function. Many orthotic devices rely on buckles, belts/straps, adjustable supports, and brackets to allow the donning or doffing of the device, and for adjusting and maintaining the device's fit/support.

There are a large variety of braces available depending on the diagnosis and physical needs of the individual. These devices include a multitude of construction materials and buckling and support designs for fitting the device around the patient's trunk or peripheral area, such as the cervical and pelvic regions.

Such braces are effective in achieving spinal stability if worn properly and consistently. However, most patients have difficulty in manually adjusting the brace's belts or straps so that the brace fits tightly enough to provide adequate support and stability but not so tight that the brace itself becomes a source of pain or discomfort, or causes the disruption of circulation. This is especially true in the case of post-operative patients who are generally in pain, have a limited range of motion, and frequently lack sufficient strength to make necessary adjustments to the brace by way of the brace's buckles and straps.

U.S. Pat. No. 4,406,043 discloses a belt buckle comprising a frame and pivotable tongue that engages the perforations in a flexible belt. Buckles of this general type can be difficult and uncomfortable to operate, particularly for persons with limited strength or mobility, such as post-operative patients. To secure or release a belt or strap using this type of buckle, the belt must be over-tightened before the pivotable tongue can be inserted into, or removed from, the desired perforation. Further, because each perforation reduces the structural integrity of the belt, buckles of this type are limited to applications not requiring fine adjustments to fit.

U.S. Pat. No. 4,688,337 discloses a two-piece clasp comprising a male clasp piece having parallel resilient arms that inset and lock into corresponding slots in a receptacle clasp piece. Straps are threaded through bars on the free ends of each clasp piece. A disadvantage of buckles of this general type is that manual adjustment of the straps through the bars on the freed ends of each clap piece is difficult, particularly for post-operative patients having limited strength and range of motion.

U.S. Pat. No. 4,903,381 teaches a fastener that accepts a strap in a receiving channel wherein a spring-loaded arresting member engages a serrated region of the strap thereby preventing the withdrawal of an inserted strap. A disadvantage of fasteners or buckles of this type is that, during a patient's daily activities, it is possible for a force or pressure to be applied to the strap in the insertion direction, thereby causing the strap to be tightened unintentionally and causing pain, discomfort, or loss of circulation.

U.S. Pat. No. 376,055 discloses a buckle comprising a clasp wherein the clasp grips an inserted belt or strap. The strap or belt is released by pulling up on the free end of the clasp. A buckle having similar features is taught in U.S. Pat. No. 5,572,771. A drawback to buckles of this type is that the strap or belt can be accidentally released if the free end of the clasp is pulled open accidentally by the patient's clothing or in some other way during the patient's daily activities.

Existing orthotic devices, such as described in U.S. Pat. No. 7,371,221, immobilize the head relative to the base using a single support bracket and a single locking pin located at the back of the cervical brace. However, such devices present the problems of being difficult for the user to adjust without assistance, and accidental release of the locking pin and the accompanying loss of support. As discussed above, it is important that adjustable supports be easy to use while also preventing accidental release.

The present invention satisfies these and other needs, and provides further related advantages.

SUMMARY OF THE INVENTION

For purposes of summarizing the disclosure, exemplary embodiments of a secure adjustable orthotic device having one or more locking mechanisms have been described herein.

The present invention may be embodied in a locking mechanism for a secure adjustable orthotic device. In one embodiment, the locking mechanism comprises a base member, a locking member and a top member. The base member comprises a base portion, a first side portion and a second side portion that, together, form a longitudinal channel for receiving a free end of a strap. The locking member is pivotally attached to the base member and is pivotable between a locked position and an unlocked position. The locking member comprises a first projection extending in a first direction and a second projection connected to the first projection but extending in a second direction. The first projection of the locking member has a first surface, a second opposite surface and a third surface. The second projection has a surface that engages an inserted strap when the locking member is in the locked position. The top member is slidably attached to the base member and comprises a top portion and one or more protrusions extending toward the locking member. Longitudinal movement of the top member relative to the base member in a first locked direction causes the one or more protrusions of the top member to apply a force to the first and then the third surfaces of the first projection of the locking member, pivoting the locking member to the locked position. Assuming a strap has been inserted into the longitudinal channel, the second projection of the locking member engages the inserted strap, thereby impeding the longitudinal movement of the strap. Longitudinal movement of the top member in a second opposite direction relative to the base member causes the one or more protrusions of the top member to apply a force to the second opposite surface of the first projection of the locking member, pivoting the locking member to the unlocked position and causing the second projection of the locking member to disengage the inserted strap, thereby allowing the longitudinal movement of the strap.

In another embodiment, at least one aperture is formed in the base portion of the base member so that the locking mechanism can be attached to other objects or surfaces. For example, the locking mechanisms can be attached to an orthotic device or orthosis (commonly known as a brace or splint).

In a further embodiment, a first aperture is formed in the first side portion of the base member, and a second aperture is formed in the second side portion of the base member. The locking member comprises a first protrusion extending in a first direction and a second protrusion extending in a second opposite direction. The first protrusion of the locking member is inserted into the first aperture in the first side portion of the base member. The second protrusion of the locking member is inserted into the second aperture in the second side portion of the base member. The first and second protrusions of the locking member form a transverse axis along which the locking member is free to pivot between the unlocked and locked positions based on the longitudinal movement of the top member relative to the base member.

In another embodiment, the first and second protrusions of the locking member are spindles. The first and second protrusions can be formed from the same material as that used to form the locking member. Alternatively, the first and second protrusions can be formed by inserting a support shaft or axle made of metal or other hard substance through the locking member.

In yet another embodiment, a first slot is formed in the outer surface of the first side portion of the base member and a second slot is formed in the outer surface of the second side portion of the base member. The first and second slots are parallel to the plane of the base portion of the base member and are located near the top edges of the first and second side portions of the base member. Preferably, the first and second slots terminate prior to the longitudinal ends of the first and second side portions of the base member. In this embodiment, the top member has a first lip extending from a first side edge of the top portion of the top member in a direction perpendicular to the plane of the top portion of the top member and a second lip extending from a second side edge of the top portion of the top member in a direction perpendicular to the plane of the top portion of the top member. A first tongue is formed on the interior surface of the first lip of the top member and a second tongue is formed on the interior surface of the second lip of the top member. The first tongue formed on the interior surface of the first lip of the top member is inserted into the first slot formed in the outer surface of the first side portion of the base member and the second tongue formed on the interior surface of the second lip of the top member is inserted into the second slot formed in the outer surface of the second side portion of the base member, thereby slidably attaching the top member to the base member. Alternatively, multiple short slots can be formed on the outer surfaces of the first and second side portions of the base member and multiple corresponding tongues can be formed on the interior surfaces of the first and second lips of the top member.

In another embodiment, first and second channels are formed on the inner surfaces of the first and second side portions of the base member. The channels run parallel to the plane of the base portion and are located near the top edges of the first and second side portions. Preferably, the channels terminate prior to the longitudinal ends of the first and second side portions of the base member. In this embodiment, a first side edge of the top portion of the top member is inserted into the first channel formed on the inner surface of the first side portion of the base member, and a second side edge portion of the top portion of the top member is inserted into the second channel formed on the inner surface of the second side portion of the base member, thereby slidably attaching the top member to the base member.

In a further embodiment of the locking mechanism, the locking member is juxtaposed to the base member. In this embodiment, a majority of the locking member is located within a well formed in the top surface of the base portion of the base member so that, in the unlocked position, the locking member does not obstruct the longitudinal channel formed by the base member. Alternatively, a majority of the locking member is proximal to the top member so that, when a strap is inserted into the locking mechanism's longitudinal channel, a majority of the locking member is located between the top member and the inserted strap.

The present invention may additionally be embodied in a locking mechanism that inhibits the locking member from pivoting from a locked position to an unlocked position when tension is applied to the strap inserted into the longitudinal channel of the locking mechanism. This embodiment comprises a top member having a protrusion extending away from the plane of the top member and toward the locking member. The protrusion has a first angled surface relative to the plane of the top member and a second parallel surface relative to the plane of the top member. Longitudinal movement of the top member in a first locking direction causes initial contact between the first angled surface of the protrusion of the top member and the first surface of the first projection of the locking member. This initial contact with the first angled surface of the protrusion of the top member applies a force to the first projection of the locking member, the force having a downward vector component relative to the plane of the top member. The downward force causes the first projection of the locking member to move in a direction perpendicular to the plane of the longitudinal channel and toward the base member so that the locking member pivots to the locked position, causing the second projection of the locking member to engage a strap inserted into the longitudinal channel and thereby preventing the withdrawal of strap. Further lateral movement of the top member causes the second surface of the protrusion of the top member that is parallel to the longitudinal movement of the top member to align with a third surface of the first projection. The third surface is parallel to the second surface of the protrusion of the top member. Thus, when the top member is in the fully locked position, contact between the protrusion of the top member and the third surface of the first projection of the locking member is along a plane parallel to the longitudinal movement of the top member. If tension is applied to the strap when the top member is in the locked position, the strap will apply a force to the second projection of the locking member in the direction of the base member. This force will be communicated through the rigid structure of the locking member and its transverse pivot, causing the third surface of the first projection of the locking member to apply a force to the second surface of the protrusion of the top member in a direction away from the base member. Because the planes of the third surface of the first projection of the locking member and the second surface of the protrusion of the top member are substantially parallel to the longitudinal movement of the top member (and the force is in a direction substantially perpendicular to the longitudinal movement of the top member), the top member does not move longitudinally in the unlocking direction and thus prevents the withdrawal of the strap.

In another embodiment, the strap that can be inserted into the locking member's longitudinal channel has a series of transverse teeth on one surface. In this embodiment, the second projection of the locking member forms a pawl that is shaped to engage the transverse teeth of an inserted strap.

The present invention may also be embodied in an adjustable orthotic device comprising a first brace portion, a second brace portion, a third brace portion, a bracket portion, and an adjustment tool. The bracket portion interconnects the first brace portion and second brace portion, and is fixedly attached to the first brace portion and slidably attached to the second brace portion. The bracket portion comprises first and second parallel projections, each projection having a plurality of apertures longitudinally spaced along a portion of its length. The second brace portion comprises a body portion and a pair of locking members attached to the body portion and spaced apart from one another. The first and second locking members of the second brace portion each has a top portion having an aperture, a first side portion and a second side portion together forming a longitudinal channel adapted to receive the first and second projections of the bracket portion respectively. Each locking member also has a pin having a diameter smaller than the aperture in the top portion of the locking member. The pin has a first end sized to fit within each of the apertures of the projections of the bracket portion (the pin being slidable in a first locked direction and a second unlocked direction along an axis defined by the longitudinal axis of the pin's shaft. The pin further has a first projection proximate to the first end of the pin and defining an axis substantially perpendicular to the longitudinal axis of the pin, a second opposite end having a second projection defining an axis substantially parallel to the first projection, and a spring that applies a force to the first projection of the pin in the locked direction. The third brace portion is detachably coupled to the first and second brace portions. The adjustment tool comprises a body portion, a first end portion, and a second end portion. The first and second end portions are spaced apart from one another. The first and second end portions each has a slot defining an axis and a first pair of surfaces adjacent to the slot, wherein surface is tapered in a direction parallel to the axis of the slot. The slots of the first and second end portions of the adjustment tool are oriented to accept the second ends of the pins of the locking members. As the first and second end portions of the adjustment tool are pushed toward the second ends of the pins, the tapered surfaces adjacent to each slot of the adjustment tool apply a force to the lips of the pins. This force is greater than the force applied by the springs, thereby causing the pins to move in the second unlocked direction. When the first and second ends of the adjustment tool are fully inserted under the lips of the two pins of the locking members, the first ends of the pins withdraw from the apertures of the first and second projections of the bracket portion, allowing the bracket portion (and the first brace portion fixedly attached thereto) to be adjusted relative to the second brace portion.

The present invention is additionally embodied in a locking mechanism wherein the first brace portion is a mandibular support, the second brace portion is a front sternum plate, and the third brace portion is a occipital-scapular plate.

These and other features and advantages of the present invention will be more readily apparent from the detailed description of the embodiments set forth below taken in conjunction with the accompanying drawings.

BRIEF DESCRIPTION OF THE DRAWINGS

Embodiments of the present invention will now be described, by way of example only, with reference to the following drawings.

Exemplary embodiments and their advantages are best understood by referring to the detailed descriptions that follow. It should be appreciated that like reference numerals are used to identify like elements illustrated in one or more of the figures, wherein showings therein are for purposes of illustrating exemplary embodiments and not for purposes of limiting the same.

DETAILED DESCRIPTION OF THE PREFERRED EMBODIMENTS

Figure 1A:
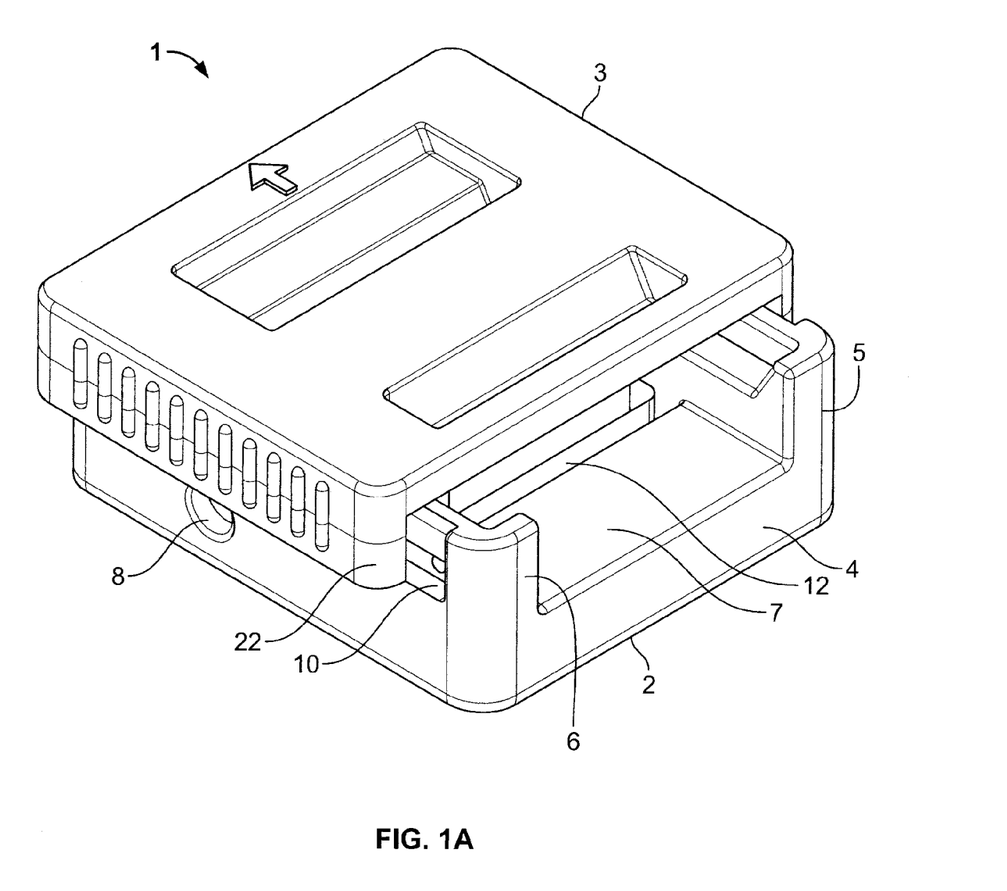
FIG. 1A is perspective view of a locking mechanism, in accordance with an embodiment of the present invention.
Figure 1B:
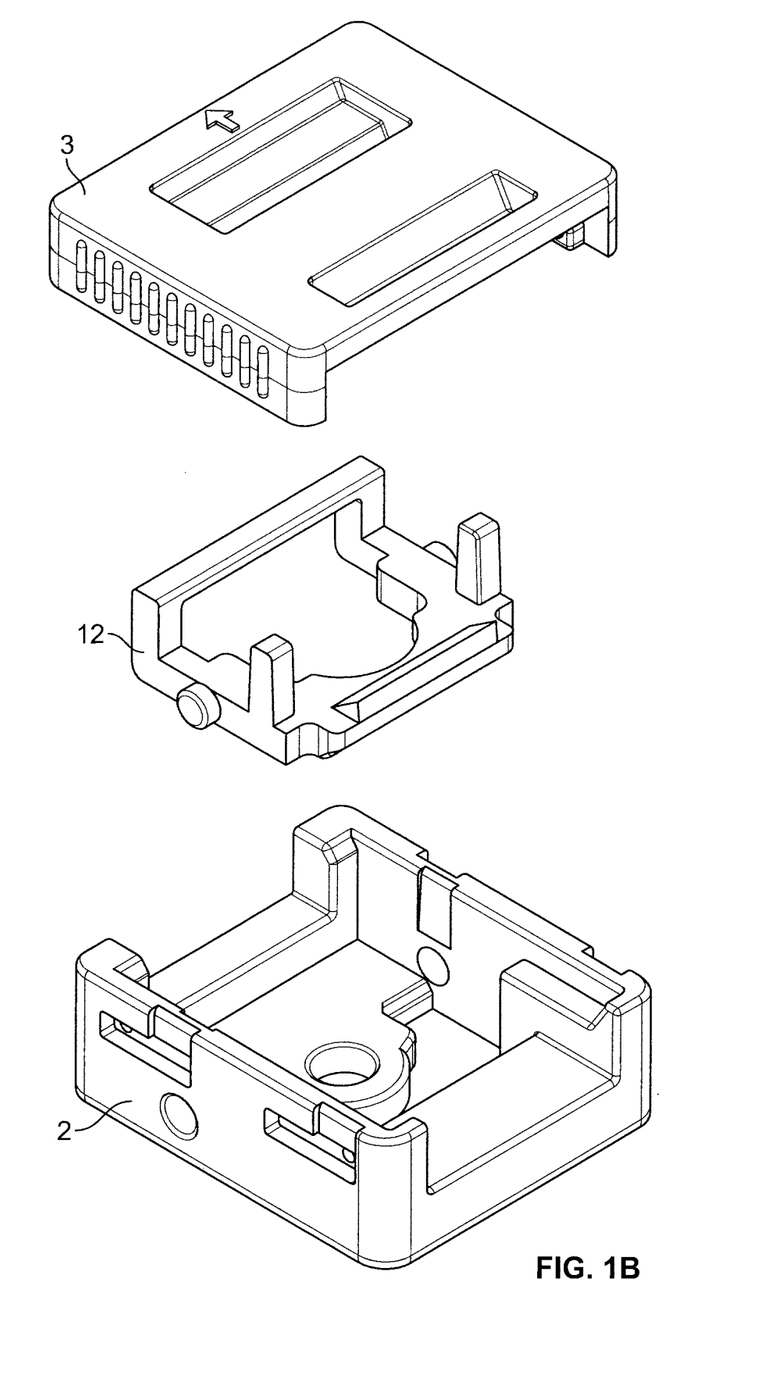
FIG. 1B is an exploded view of the locking mechanism shown in FIG. 1A.

Referring now to the drawings in detail, FIGS. 1A and 1B FIG. 1 show a representative locking mechanism 1 according to the present invention comprising a base member 2, a locking member 12, and a top member 3.

Figure 2:
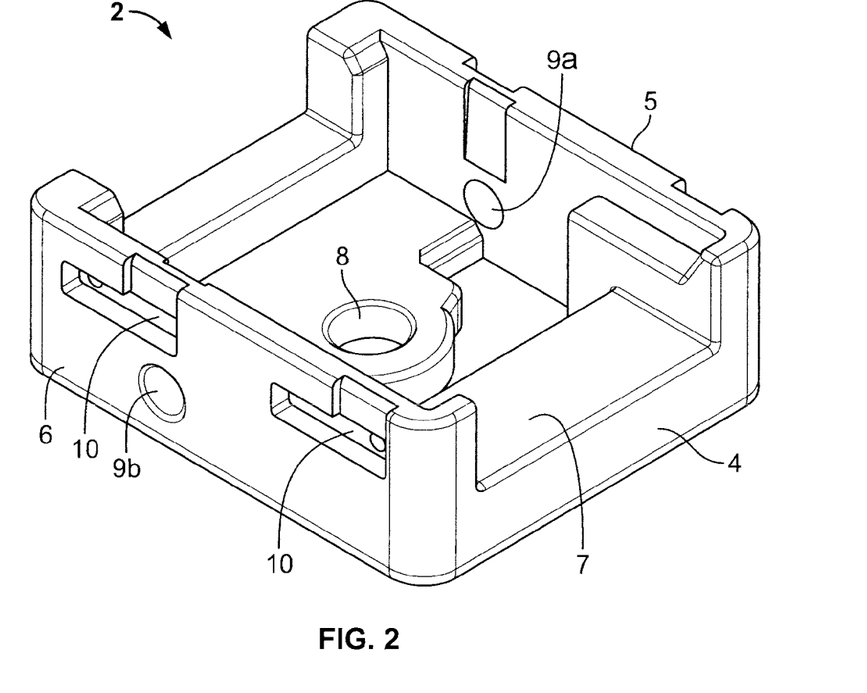
FIG. 2 is an enlarged perspective view of a base member, in accordance with an embodiment of the present invention.

Referring to FIGS. 1A and 2, the base member 2 is formed by a base portion 4, a first side portion 5 and a second side portion 6 that form a longitudinal channel 7 for receiving a free end of a strap 31 (shown in FIGS. 2A through 2C). In this embodiment of the base member, at least one aperture 8 is formed in the base portion of the base member to allow the locking mechanism to be attached to other objects, such as an orthotic device. A first aperture 9 is formed in the first side portion 5 of the base member, and a second aperture 8 is formed in the second side portion 6 of the base member. A well 11 is formed in the top surface of the base portion of the base member to accommodate the locking member 12. A plurality of slots 10 are formed in the outer surfaces of the first and second side portions of the base member. The slots are parallel to the plane of the base portion 4 of the base member and terminate prior to the longitudinal ends of the first and second side portions of the base member.

Figure 3:
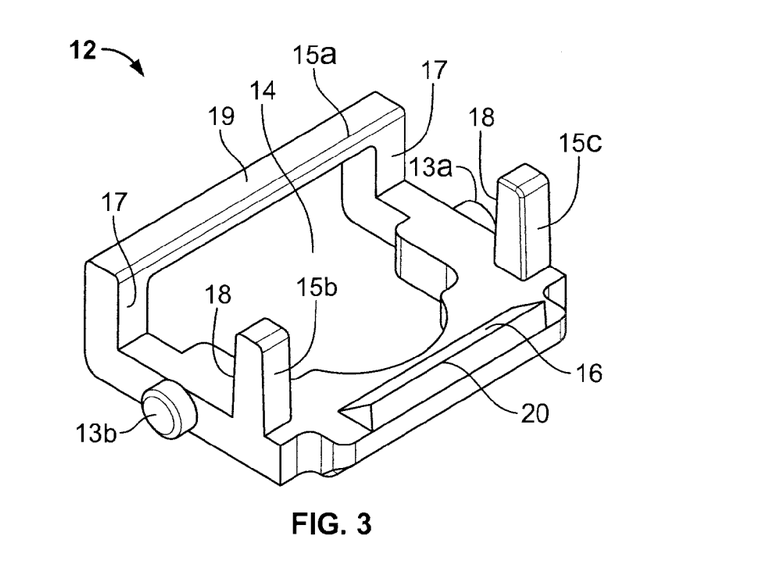
FIG. 3 is an enlarged perspective view of a locking member, in accordance with an embodiment of the present invention.

As shown in FIGS. 1B and 3, the locking member 12 comprises a plurality of first projections 15*a*, 15*b*, and 15*c* extending in a first direction and a second projection 16 connected to the plurality of first projections but extending in a second direction. The first projection 15*a* of the locking member has a first surface 17 and a third surface 19. The first projections 15*b* and 15*c* have second opposite surfaces 18. The second projection 16 has a surface 20 capable of engaging an inserted strap 31 (shown in FIGS. 2A through 2C) when the locking member 12 is pivoted to, or is in, the locked position. A first finger 13*a* of the locking member shown in FIG. 3 extends in a first direction and a second finger 13*b* extends in a second opposite direction. The first and second protrusions of the locking member form a transverse rotational axis.

In order to pivotally attach the locking member 12 to the base member 2, the first finger 13*a* of the locking member is inserted into the first aperture 9*a* in the first side portion 5 of the base member, and the second finger 13*b* of the locking member is inserted into the second aperture 9*b* in the first side portion 5 of the base member. The first and second protrusions of the locking member form a transverse axis along which the locking member is free to pivot between an unlocked and a locked position.

Figure 4A:
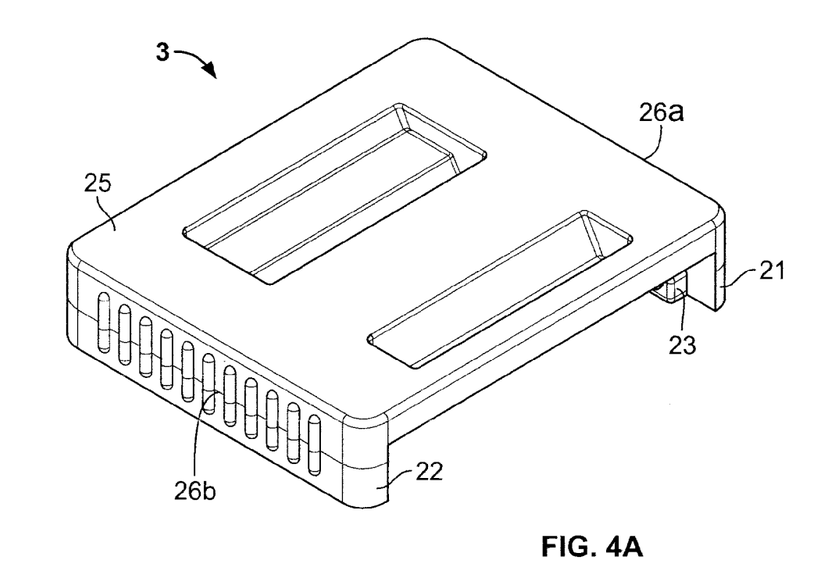
FIGS. 4A and 4B are enlarged top and bottom perspective views of a top member, in accordance with an embodiment of the present invention.
Figure 4B:
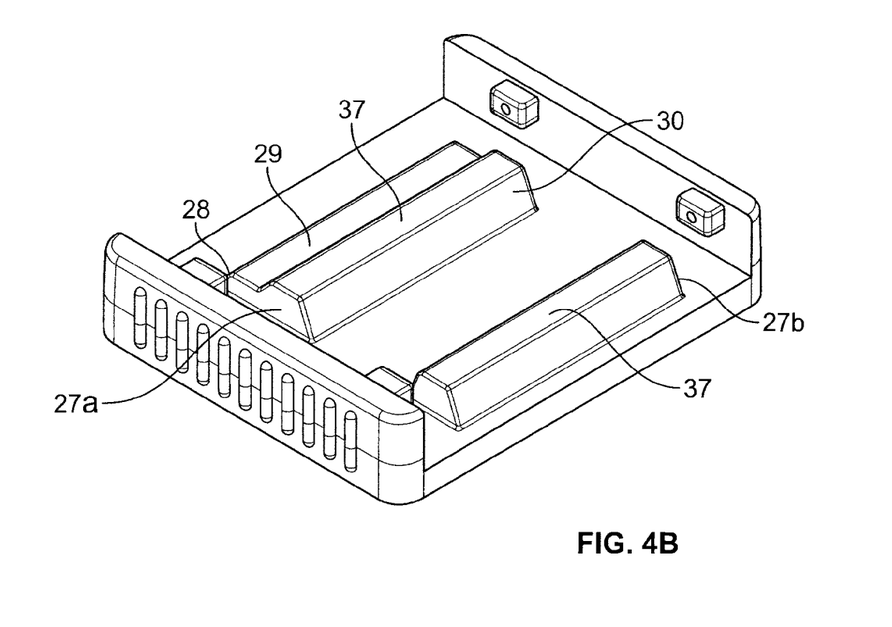

FIGS. 4A and 4B show a top member 3 having a top portion 25, a first lip 21 extending from a first side edge 26*a* of the top portion of the top member in a direction perpendicular to the plane of the top member and a second lip 22 extending from a second side edge 26*b* of the top portion of the top member in a direction perpendicular to the plane of the top member. A plurality of first tongues 23 are formed on the interior surface of the first lip 21 of the top member, and a plurality of second tongues 24 are formed on the interior surface of the second lip 22 of the top member.

FIG. 4B shows the bottom surface of top member 3. A first protrusion 27*a* and a second protrusion 27*b* are formed on the inner surface of the top portion of the top member. The first protrusion 27*a* has an angled first surface 28 (relative to the plane of the longitudinal movement of the top member), a second surface 29 that is parallel to the plane of the longitudinal movement of the top member, and a third surface 30. The first and second protrusions each also has a strap alignment surface 37.

According to the embodiment shown in FIG. 1, in order to slidably attach the top member 3 to the base member 2, the first tongues 23 formed on the interior surface of the first lip 21 of the top member are inserted into the plurality of first slots 10*a* formed in the outer surface of the first side portion 5 of the base member. The second tongues 24 formed on the interior surface of the second lip 22 of the top member are inserted into the plurality of second slots 10*b* formed in the outer surface of the second side portion 6 of the base member.

In another embodiment, first and second channels are formed on the inner surfaces of the first and second side portions of the base member. The channels run parallel to the plane of the base portion and are located near the top edges of the first and second side portions. Preferably, the channels terminate prior to the longitudinal ends of the first and second side portions of the base member. In this embodiment, a first side edge of the top portion of the top member is inserted into the first channel formed on the inner surface of the first side portion of the base member, and a second side edge portion of the top portion of the top member is inserted into the second channel formed on the inner surface of the second side portion of the base member, thereby slidably attaching the top member to the base member.

Figures 5A, 5B, 5C:
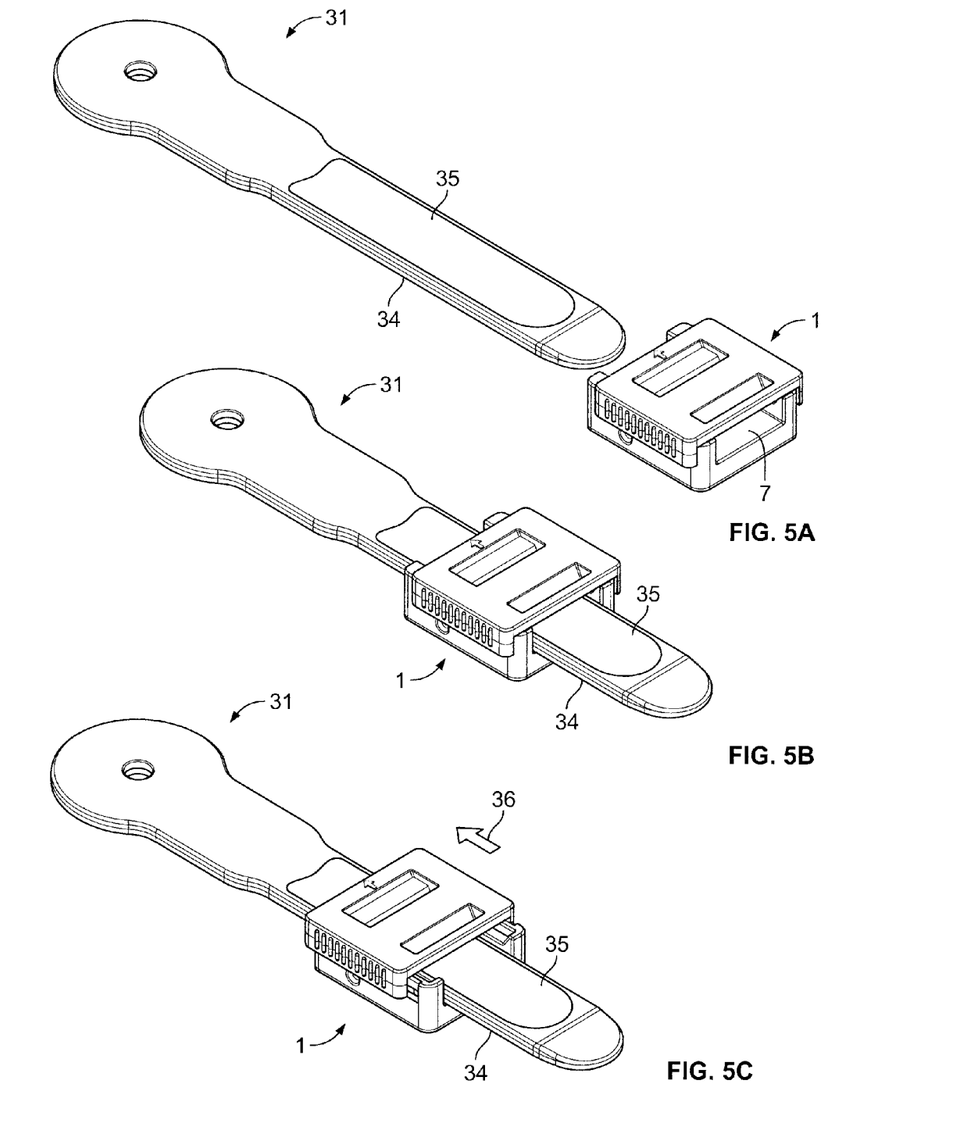
FIGS. 5A through 5C inclusive are perspective views that show, respectively, (i) a strap prior to insertion into one of the locking mechanisms shown in FIG. 1, (ii) the strap inserted into the locking mechanism, wherein the locking mechanism is in the unlocked position, and (iii) the strap inserted into the locking mechanism, wherein the locking mechanism is in the locked position.

FIGS. 5A through 6B show an assembled embodiment of the locking mechanisms 1 as it relates to a strap 31. FIGS. 5A and 5B show the strap 31 prior to, and following, insertion into the longitudinal channel 7, wherein the top member 3 is in the unlocked position. The strap 31 is generally planar in shape, having first 34 and second 35 opposed major surfaces. The first major surface 34 of the strap 31 includes a series of longitudinally spaced transverse locking teeth 32 (see FIGS. 6A-6B). FIG. 5C shows the strap inserted into the longitudinal channel 7 and the top member 3 in the locked position.

Figure 6A:
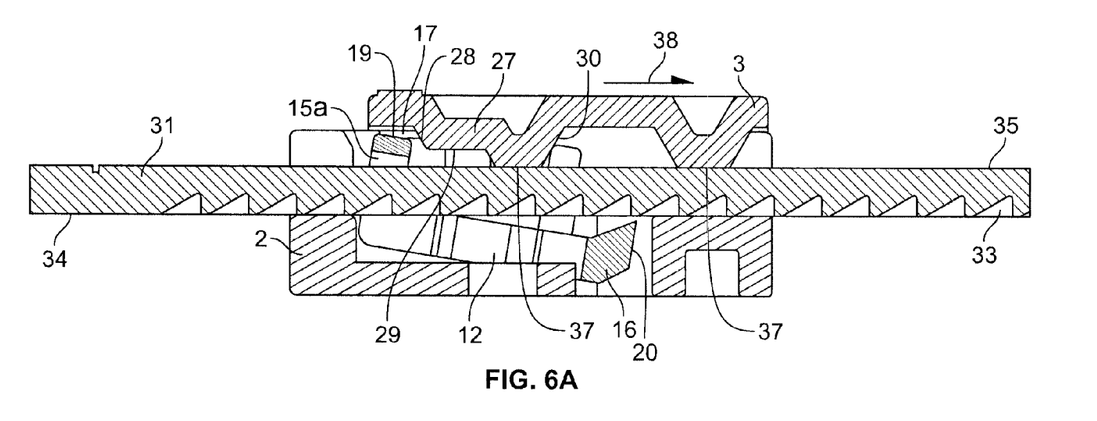
FIGS. 6A and 6B are cross-sectional views of the locking mechanisms of FIGS. 5B and 5C, respectively.

FIG. 6A shows a longitudinal cross-sectional view of the embodiment of the locking mechanism shown in FIG. 5B. Specifically, longitudinal movement of the top member 3 relative to the base member 2 in the "unlocked" direction 38 causes the third surface 30 of the first protrusion 27*a* of the top member to apply a force to the second opposite surfaces 18 of the first projections 15*b* and 15*c* of the locking member 12. The force applied to surfaces 18 causes the locking member to pivot about its transverse axis, defined by fingers 13*a* and 13*b*, to the unlocked position, wherein the second projection 16 pivots into the well 11 in the bottom portion 4 of the base member 2 so that the second projection 16 does not inhibit the insertion or adjustment of the strap 31 in the longitudinal channel 7.

Figure 6B:
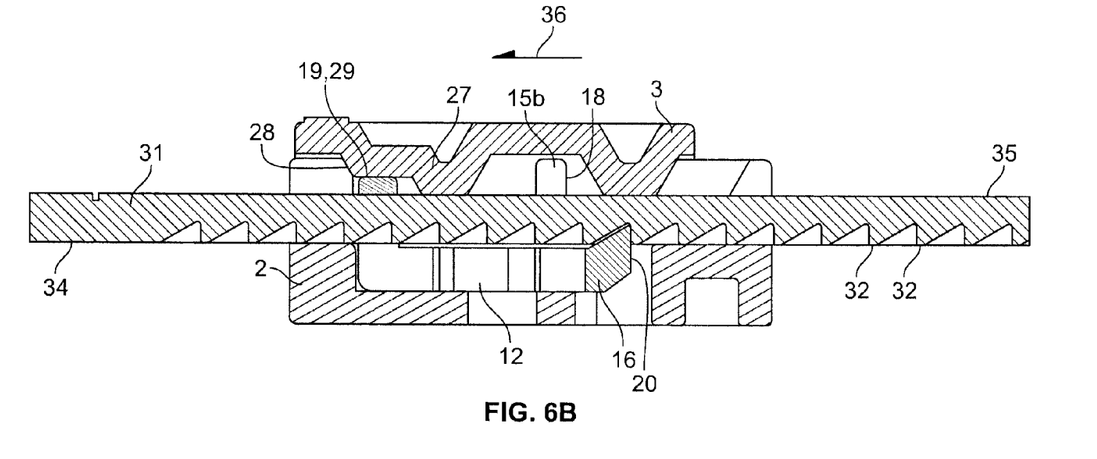

As shown in FIG. 6B, which is a longitudinal cross-sectional view of the embodiment of the locking mechanism and strap shown in FIG. 5C, longitudinal movement of the top member 3 relative to the base member 2 in the "locked" direction 36 causes the first protrusion 27*a* of the top member to apply a force to the first surface 17 of the first projection 15*a* of the locking member, pivoting the locking member to the locked position. In the locked position, the pawl 20 of the second projection 16 of the locking member engages the inserted strap 31 and the strap alignment surfaces 37 of the first and second protrusions of the top member 3 prevent the strap from deflecting away from the pawl 20 thereby impeding the withdrawal of the strap. Specifically, longitudinal movement of the top member in the locked direction 36 causes initial contact between the angled first surface 28 of the first protrusion 27*a* and the first surface 17 of the first projection 15*a* of the locking member 12. Continued movement of the top member in the locked direction 36 causes the first surface 28 of the protrusion to apply a force to the first projection 15*a* of the locking member. Due to the angle of the first surface 28, the force applied to the first projection 15*a* has a downward vector component (toward the base member). The applied force causes the locking member to pivot to the locked position, causing the second projection 16 of the locking member to engage a strap 31 inserted into the longitudinal channel 7, thereby preventing the withdrawal of strap. In the embodiment of the locking mechanism shown in FIG. 6B, the second projection 16 of the locking member 12 forms a pawl having a free end 20 shaped to fit the longitudinal spaces 33 between the transverse locking teeth 32 on the first surface 35 of the strap 31. When the locking member pivots from the unlocked to the locked position following the insertion of a strap, the free end enters the longitudinal space between adjacent transverse locking teeth, thereby obstructing the withdrawal of the strap.

FIG. 6B also illustrates that the present invention may be additionally embodied in a locking mechanism that inhibits the accidental movement or release of the strap 31 when the top member 12 is in the fully locked position because the application of a longitudinal force to the strap in either direction will not cause the top member to move in the unlocked direction 35. Specifically, when the top member in the fully locked position, the second surface 29 of the first protrusion 27a aligns with the third surface 19 of the first projection 15a of the locking member. The aligned surfaces 29 and 19 are parallel to one another and parallel to the plane of the longitudinal movement of the top member 12. Therefore, attempting to withdraw or insert the strap 31 while the locking mechanism is in the fully locked position creates a force that does not result in movement at surfaces 29 and 19 because the generated force is in a direction perpendicular to the longitudinal movement in which the top member is free to engage.

Figure 7:
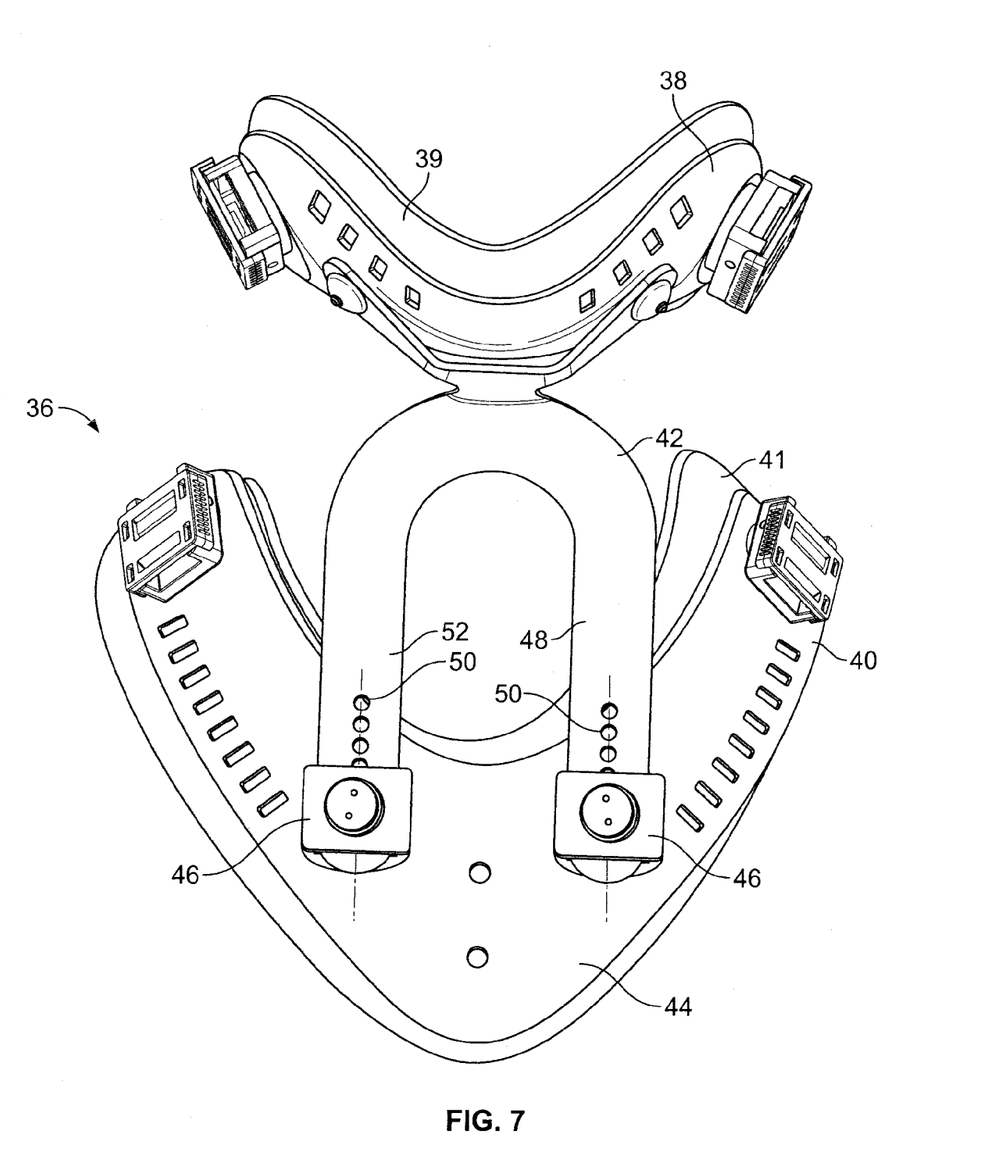
FIG. 7 is a perspective view of an orthotic device having secure adjustable supports, in accordance with an embodiment of the present invention.

FIG. 7 shows an orthotic device 36 having secure adjustable supports according to the present invention. The orthotic device comprises a first brace portion 38 forming a mandibular support, a second brace portion 40 forming a front sternum plate, and a bracket portion 42 fixedly attached to the first brace portion and slidably attached to the second brace portion. The first brace portion 38 and second brace portion 40 each comprises a cushioned pad 39 and 41 respectively. The second brace portion 40 further comprises a body portion 44, and a pair of locking members 46 spaced apart from one another. The bracket portion 42 comprises a first projection 48 defining an axis and a second projection 52 spaced apart from the first projection and defining an axis that is parallel to the axis defined by the first bracket 42. The first projection 48 and second projection 52 of the bracket portion 42 each has a plurality of apertures 50 longitudinally spaced along a portion of their length.

Figure 8:
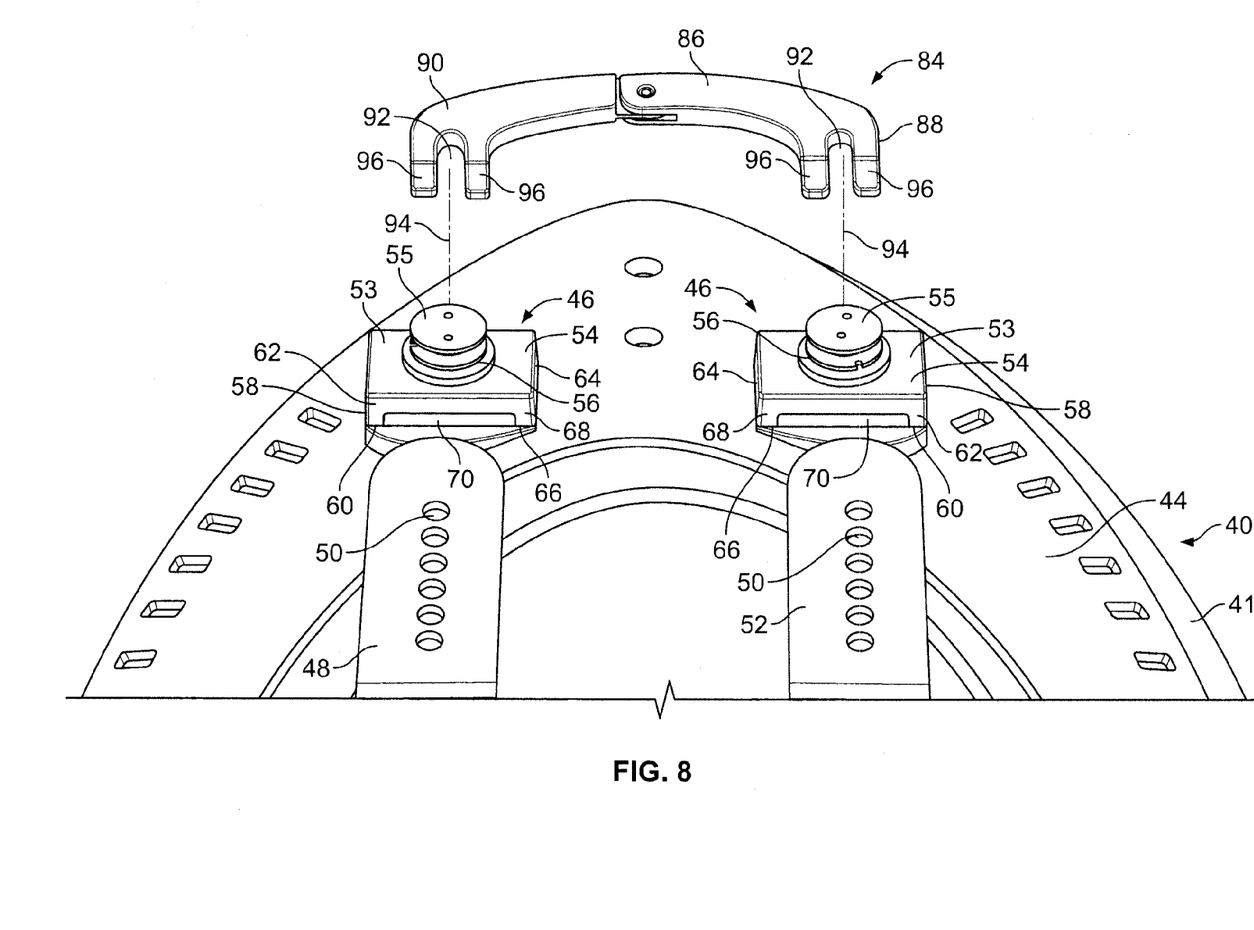
FIG. 8 is a perspective view of a portion of the secure adjustable orthotic device and an adjustment tool, in accordance with an embodiment of the present invention.

FIG. 8 is a perspective view of a portion of the second brace portion 40, the first and second projections of the bracket portion 42, and an adjustment tool 84. The second brace portion includes the pair of locking members 46. Each locking member comprises a housing 53 and a locking portion 55. The housing 53 of each locking member comprises a top portion 54 having an aperture 56, a first side portion 58 having a first end 60 attached to the body portion 44 of the second brace portion and a second opposite end 62 attached to the top portion 54 of the locking member, and a second side portion 64 having a first end 66 attached to the body portion 44 of the second brace portion and a second opposite end 68 attached to the top portion 54 of the locking member. The top portion 54, first side portion 58, and second side portion 64 of each locking portion housing 53 form a longitudinal channel 70 configured to receive one of the first projection 48 or second projection 52 of the bracket portion 42.

The adjustment tool 84 comprises a body portion 86 having a first end portion 88 and a second end portion 90 that is spaced apart from the first end portion. The first and second end portions of the adjustment tool 84 each has a slot 92 defining an axis 94, and a pair of surfaces 96 adjacent to the slot. The surfaces 96 are tapered in a direction parallel to the axis 94. And because the first projection 50 and second projection 52 of the bracket 42 secure the first brace portion 38 to the second brace portion 40 at two independent locking members 46, adjustment requires the use of the adjustment tool 84, thereby reducing the chance of accidental movement of the first brace portion relative to the second brace portion.

Figure 9:
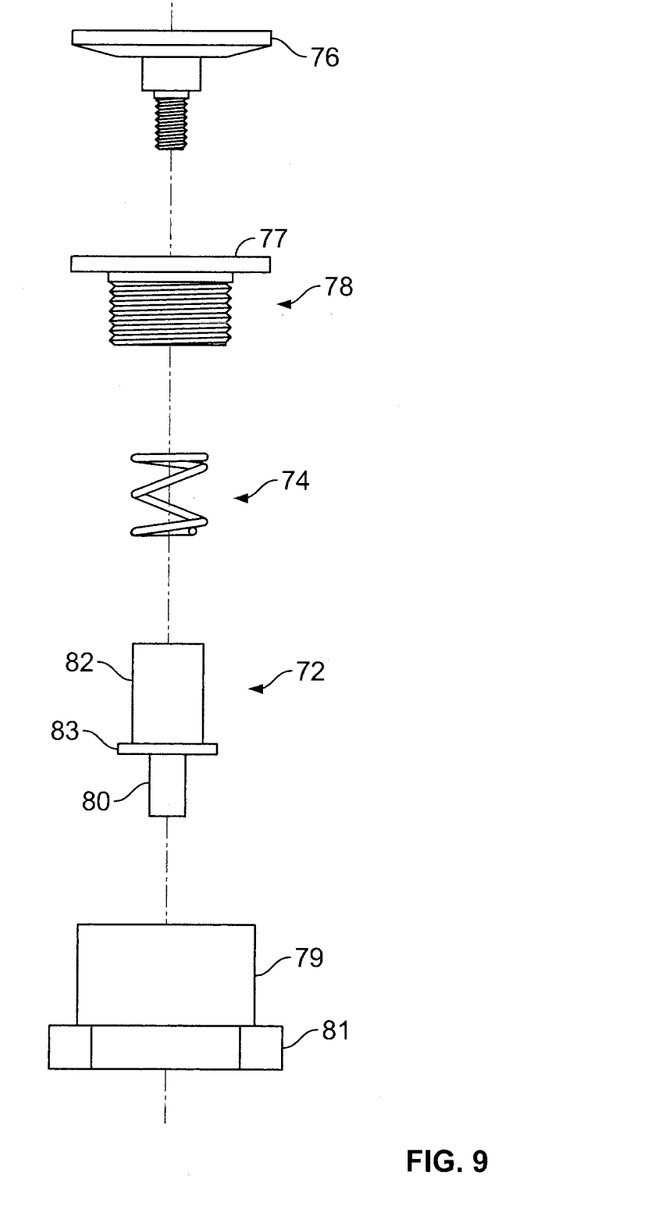
FIG. 9 is an exploded view a locking member removed from a locking mechanism housing of a second brace portion of the secure adjustable orthotic device shown in FIG. 8.

FIG. 9 is an exploded view of a locking portion 55 extracted from the housing 53 of a locking member 46 of the second brace portion 40 shown in FIGS. 7 and 8. Each locking portion 55 comprises a pin 72, a coiled spring 74, an annular disc 76, a cap 78, and a body portion 79. The pin 72 comprises a first end 80, a second opposite end 82, and an annular lip 83 wherein the annular lip has an outer diameter larger than the inner diameter of the coiled spring 74. The first end 80 of the pin is sized to fit within the apertures 50 of the projections 48 and 52 of the bracket portion 42. The cap 78 has an aperture 77 formed in the center of its top and the body portion 79 has an aperture 81 formed in the center of its base. The second end 82 of the pin 72 has a diameter smaller than the diameter of the aperture 77 formed in the center of the top of the cap 78.

When assembled, the second end 82 of the pin 72 is positioned within the coiled spring 74 with the coiled spring abutting the annular lip 83 of pin 72. The second end of the pin is inserted through the aperture 77 in the top of the cap 78 and the annular disc 76 is coupled to the second end 82 of the pin 72. The body portion 79 is then fixedly attached to the cap 78. The first end 80 of the pin 72 is allowed to project through the aperture 81 in the center of the base of the body portion 79. thereby enclosing the coiled spring and majority of the pin 72. The second end 82 of the pin 72 is positioned within the fixedly attached within the aperture of the second annular disc 78 so that the second annular disc is positioned between the first end 80 and the second end 82 of the pin. The pin 72 of each locking portion is positioned through the aperture 56 formed in the top portion 54 of the housing 53. The pin is slidable between a first locked position and a second unlocked position along a longitudinal axis defined by the shaft of the pin 72 and substantially perpendicular to the plane of the top portion 54 of the housing 53 of the locking member 46. When the locking portion 55 is contained within the housing 53 of the locking member 46, and the pin 72 is in the locked position, its first end 80 extends into the longitudinal channel 70 of the housing 53. When the pin 72 is in the unlocked position, its first end 80 is retracted from the longitudinal channel 70 of the housing. The coiled spring 74 resists compression between the annular lip 83 of the pin 72 and the cap 78 thereby applying a force to the pin 72 in the locked position.

Figure 10A:
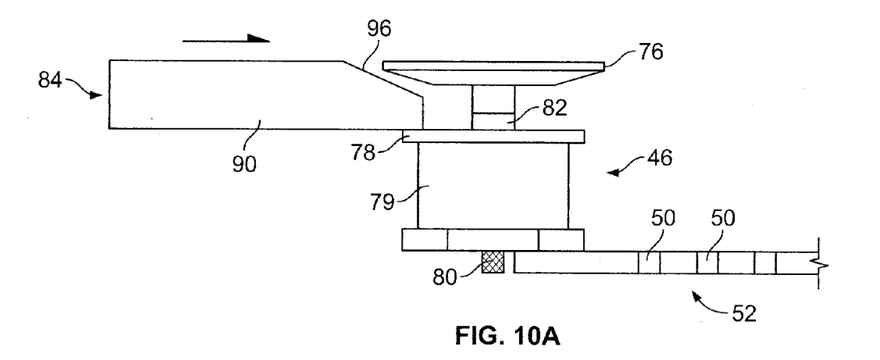
FIGS. 10A-10C are side views of an assembled locking member shown in FIG. 9, along with an adjustment tool and a bracket portion of the secure adjustable orthotic device, in accordance with an embodiment of the present invention.
Figure 10B:
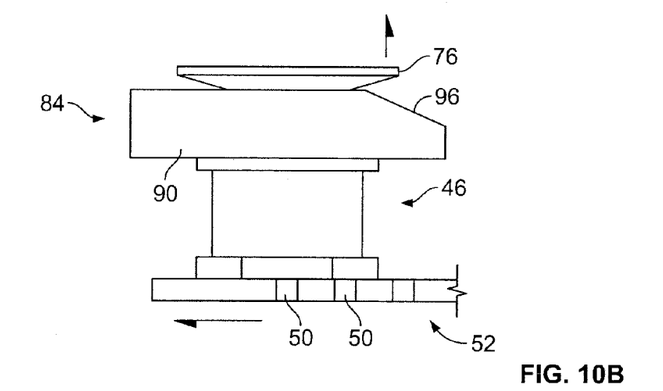
Figure 10C:
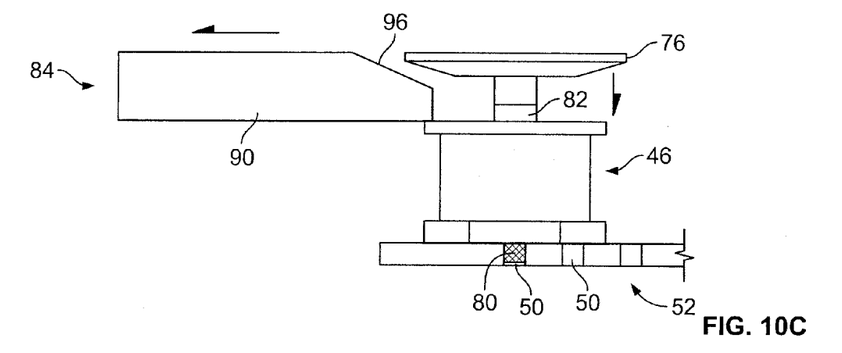

FIGS. 10A-10C are side views of an assembled locking portion 55 extracted from the housing 53 of a locking member 46 of the second brace portion 40 shown in FIGS. 7-8. FIG. 10A shows the locking portion 55 with the annular disc 76 and pin 72 in the locked position with a second end portion 90 of the adjustment tool 84 approaching the locking portion from the left of the figure (it should be apparent that all depictions of the second end portion 90 of the adjustment tool 84 are equally representative of the first end portion 88 of the adjustment tool). Also shown in FIG. 10A is a longitudinal cross section of the second projection 52 of the bracket portion 42 to illustrate the plurality of apertures 50 longitudinally spaced along a portion of the second projection's length (it should be apparent that all depictions of the second projection 52 of the bracket portion 42 are equally representative of the first projection 48 of the bracket portion).

FIG. 10B shows the annular disc 76 and pin 72 of the locking portion 55 in the unlocked position. Due to the angle of the tapered surface 96 of the second end portion 90 of the adjustment tool 84, insertion of the adjustment tool between the annular disc 76 and the cap 78 exerts a force on the bottom of the annular disc 76 that has an upward component. When the upward component of the force applied to the annular disc 76 (and the pin 72 to which the annular disc is coupled) by the insertion of the adjustment tool 84 overcomes the opposite force that the coiled spring 74 applies to the annular lip 83 of the pin 72 (and the annular disc 76 to which it is coupled) due to the coiled spring's resistance to compression, the annular disc 76 and pin 72 slide to the unlocked position. As shown in FIG. 10B, when the annular disc 76 and pin 72 are in the unlocked position, the first end 80 of the pin retracts. When the locking portion 55 is contained within the housing 53 of the locking member 46 and the pin 72 is in the unlocked position, the first end 80 of the pin 72 is retracted from the longitudinal channel 70 of the housing 53. With the first end 80 of the pin 72 retracted from the longitudinal channel 70, the second projection 52 of the bracket portion 42 can be inserted into, or adjusted within, the longitudinal channel 70.

FIG. 10C shows the second end portion 90 of the adjustment tool 84 removed from between the annular disc 76 and the cap 78 of the locking portion 55. With the adjustment tool removed, the force applied by the compressed coiled spring 74 to the annular lip 83 of the pin 72 causes the pin to return to the locked position. When the locking portion 55 is contained within the housing 53 of the locking member 46, and the pin 72 returns to the locked position, its first end 80 extends into the longitudinal channel 70 of the housing 53. With the second projection 52 of the bracket portion 42 positioned within the longitudinal channel, the first end 80 of the pin 72 can enter one of the plurality of apertures 50 longitudinally spaced along a portion of the second projection 52 of the bracket portion 42 thereby preventing the accidental movement of the bracket portion 42 (and the first brace portion 38 to which it is fixedly attached) relative to the second brace portion 40 as show in FIG. 7.

The present invention has been described above in terms of presently preferred embodiments so that an understanding of the present invention can be conveyed. However, there are other embodiments not specifically described herein for which the present invention is applicable. Therefore, the present invention should not to be seen as limited to the forms shown, which are illustrative rather than restrictive.

What is claimed is:

1. A locking mechanism comprising:
a base member having a longitudinal channel for receiving a free end of a strap, the base member comprising
a base portion,
a first side portion connected to the base portion, and
a second side portion connected to the base portion,
wherein the base portion, first side portion and second side portion form the longitudinal channel;
a locking member pivotally attached to the base member and pivotable between a locked position and an unlocked position, wherein the locking member comprises
a first projection extending in a first direction, and having a first surface and a second opposite surface, and
a second projection connected to the first projection and extending in a second direction,
wherein the second projection has a first surface configured to engage the free end of the strap when the locking member is in the locked position; and
a top member slidably attached to the base member, the top member comprising:
a top portion, and
one or more protrusions formed in the top portion and extending toward the locking member;
wherein longitudinal movement of the top member relative to the base member in a first direction causes the one or more protrusions of the top member to apply a force to the first surface of the first projection of the locking member, pivoting the locking member to the locked position;
wherein, in the locked position, the first surface of the second projection of the locking member is configured to engage the free end of the strap, thereby impeding the withdrawal of the strap;
wherein longitudinal movement of the top member in a second opposite direction relative to the base member causes the one or more protrusions of the top member to apply a force to the second opposite surface of the first projection of the locking member, pivoting the locking member to the unlocked position; and
wherein, in the unlocked position, the first surface of the second projection of the locking member is configured to disengage the free end of the strap, thereby allowing the withdrawal of the strap.

2. The locking mechanism according to claim 1, wherein an aperture is formed in the base portion of the base member for fixedly coupling the locking mechanism to an orthotic device.

3. The locking mechanism according to claim 1, wherein:
the locking member comprises a first protrusion extending in a first direction and a second protrusion extending in a second opposite direct;
the first protrusion of the locking member is inserted into a first aperture in the first side portion of the base member; and
the second protrusion of the locking member is inserted into a second aperture in the second side portion of the base member.

4. The locking mechanism according to claim 3, wherein the first and second protrusions of the locking member are spindles formed from the same material as that used to form the locking member.

5. The locking mechanism according to claim 3, wherein the first and second protrusions are formed by inserting an axle transversely through the locking member.

6. The locking mechanism according to claim 1, wherein:
the base member further comprises
a first side portion including a first slot formed in the outer surface of the first side portion, and
a second side portion including a second slot formed in the outer surface of the second side portion;
the top member further comprises
a first lip extending from a first edge of the top portion of the top member, wherein a first tongue is formed on the inner surface of the first lip, and
a second lip extending from a second opposite edge of the top portion of the top member, wherein a second tongue is formed on the inner surface of the second lip; and
wherein the first and second tongues of the top member are inserted into the first and second slots formed in the outer surfaces of the first and second side portions of the base member, thereby slidably attaching the top member to the base member.

7. The locking mechanism according to claim 6, wherein:
the first and second slots formed in the outer surfaces of the first and second side portions of the base member are parallel to the plane of the base portion of the base member, and are located near the top edges of the first and second side portions of the base member; and
the first and second slots terminate prior to the longitudinal ends of the first and second side portions of the base member.

8. The locking mechanism according to claim 7, wherein a plurality of the slots are formed on the outer surface of each of the first and second side portions of the base member.

9. The locking mechanism according to claim 7, wherein:
a plurality of the tongues are formed on the inner surfaces of each of the first and second lips of the top member; and
the location of the plurality of tongues formed on the first and second lips of the top member correspond to the plurality of slots on the first and second side portions of the base member.

10. The locking mechanism according to claim 1, wherein:
the base member further comprises
    a first side portion including a first channel formed in the inner surface of the first side portion, and
    a second side portion including a second channel formed in the inner surface of the second side portion;
the top member further comprises
    a first edge, and
    a second opposite edge; and
wherein the first and second edges of the top member are inserted into the first and second channels formed in the inner surfaces of the first and second side portions of the base member, thereby slidably attaching the top member to the base member.

11. The locking mechanism according to claim 1, wherein:
the first and second channels formed in the inner surfaces of the first and second side portions of the base portion are parallel to the plane of the base portion of the base member, and are located near the top edges of the first and second side portions of the base member; and
the first and second channels terminate prior to the longitudinal ends of the first and second side portions of the base member.

12. The locking mechanism according to claim 1, wherein the second projection of the locking member is contained within a well formed in the top surface of the base portion of the base member when the top member is in the unlocked position.

13. The locking mechanism according to claim 1, wherein the locking member is adjacent to the top member.

14. The locking mechanism according to claim 1, wherein:
the protrusion of the top member comprises
    a first surface that is angled relative to the plane of the top member, and
    a second surface that is parallel to the plane of the top member and the longitudinal movement of the top member;
the first projection of the locking member comprises a third surface that is substantially parallel to the second surface of the protrusion of the top member;
wherein initial longitudinal movement of the top member in the first locking direction causes the first surface of the protrusion of the top member to contact the first surface of the first projection of the locking mechanism, thereby applying a force to the first projection of the locking member, wherein the force has a vector component directed at the base member; and
wherein complete longitudinal movement of the top member in the first locking direction causes the second surface of the protrusion of the top member to align with the third surface of the first projection of the locking member.

15. The locking mechanism according to claim 1, wherein:
a strap is provided having a planar shape and a plurality of transverse teeth longitudinally spaced along one major surface of the strap; and
the second projection of the locking member forms a pawl shaped to allow the second projection to engage the transverse teeth of the strap when the strap is inserted into the longitudinal channel and the locking member is pivoted into a locked position.

16. A locking mechanism comprising:
a base member having a longitudinal channel for receiving a free end of a strap, the base member comprising
    a base portion,
    a first side portion connected to the base portion, and
    a second side portion connected to the base portion,
    wherein the base portion, first side portion and second side portion form the longitudinal channel;
a locking member comprising
    a first projection extending in a first direction, wherein the first projection has a first surface and a second opposite surface, and
    a second projection connected to the first projection and extending in a second direction;
a top member comprising
    a top portion, and
    one or more protrusions formed in the top portion and extending toward the locking member;
means for pivotally attaching the locking member to the base member so that the locking member is pivotable between a locked position and an unlocked position;
means for slidably attaching the top member to the base member so that the top member is slidable between a locked position and an unlocked position;
means for inhibiting the withdrawal of the strap; and
means for allowing the withdrawal of the strap.

17. The locking mechanism of claim 16, wherein the means for inhibiting the withdrawal of the strap prevents the top member from sliding from the locked position to the unlocked position when lateral forced is applied to a strap inserted into the longitudinal channel.

* * * * *